United States Patent [19]

Mustacich et al.

[11] 4,343,788
[45] Aug. 10, 1982

[54] ANTIMICROBIAL POLYMER COMPOSITIONS

[75] Inventors: Robert V. Mustacich; Donald S. Lucas; Roger L. Stone, all of Fairfield, Ohio

[73] Assignee: The Procter & Gamble Company, Cincinnati, Ohio

[21] Appl. No.: 53,619

[22] Filed: Jun. 29, 1979

[51] Int. Cl.$^3$ ............................................. A61K 31/74
[52] U.S. Cl. .................................................... 424/78
[58] Field of Search ................... 128/348, 130, 213 A, 128/213 R, 214 R, 214.2, 214.4, 221, 260, 349, 1 R; 474/78, 81; 260/185; 424/184

[56] References Cited

U.S. PATENT DOCUMENTS

| | | |
|---|---|---|
| 1,772,975 | 8/1930 | Wieland . |
| 2,154,499 | 2/1940 | Hoffmann et al. ........................ 99/90 |
| 2,190,714 | 2/1940 | Hoffman et al. ........................ 99/224 |
| 2,466,663 | 4/1949 | Russ et al. ............................... 167/58 |
| 2,589,445 | 3/1952 | Sommer ................................. 424/184 |
| 2,729,586 | 1/1956 | Peck ....................................... 424/177 |
| 3,070,559 | 12/1962 | Nitzsche et al. ....................... 260/185 |
| 3,279,996 | 10/1966 | Long et al. .............................. 167/82 |
| 3,404,987 | 10/1968 | Kooistre et al. ........................ 99/180 |
| 3,434,869 | 3/1969 | Davidson ................................ 117/94 |
| 3,524,447 | 8/1970 | Evans et al. ........................... 128/348 |
| 3,566,874 | 3/1971 | Shepherd et al. ..................... 128/349 |
| 3,598,126 | 8/1971 | Wepsic .................................. 128/348 |
| 3,598,127 | 8/1971 | Wepsic .................................. 128/349 |
| 3,608,063 | 9/1971 | Banker ..................................... 424/22 |
| 3,663,965 | 5/1972 | Lee et al. ...................................... 3/1 |
| 3,695,921 | 10/1972 | Shepherd et al. ....................... 117/72 |
| 3,699,956 | 10/1972 | Kitrilakis et al. ..................... 128/348 |
| 3,708,324 | 1/1973 | Stebleton .............................. 117/47 R |
| 3,854,480 | 12/1974 | Zaffaroni ............................... 128/260 |
| 3,886,947 | 6/1975 | Sawyer .................................. 128/348 |
| 3,897,376 | 7/1975 | Lampe ................................... 260/185 |
| 3,926,705 | 12/1973 | Todd ...................................... 156/155 |
| 3,940,430 | 2/1976 | Brenner et al. ....................... 424/184 |
| 3,996,934 | 12/1976 | Zaffaroni .............................. 128/130 |
| 4,012,496 | 3/1977 | Schopflin ............................. 128/130 |
| 4,012,497 | 3/1977 | Schopflin ............................. 128/130 |

FOREIGN PATENT DOCUMENTS 2720776 11/1978 Fed. Rep. of Germany .

OTHER PUBLICATIONS

Kabara–Cosmetics & Perfumery, vol. 90, May 1975, pp. 21-25.
The Merck Index, 7th Ed., p. 1117, "Zinc Propionate".

Primary Examiner—Sam Rosen
Attorney, Agent, or Firm—Michael J. Roth; Steven J. Goldstein; Richard C. Witte

[57] ABSTRACT

The present invention relates to medical polymers and devices made therefrom, and is based on the discovery that certain carboxylate antimicrobial agents can be releasably incorporated into permeable polymers. The walls of medical devices such as catheters can be fashioned from such polymers. In use, the antimicrobial agent diffuses from the walls to the surface of the device to form an antimicrobial barrier on the surface of the device and a zone of microbial inhibition on tissue surfaces surrounding the device, thereby effectively supplementing the body's own natural microbial barriers where they have been compromised. The bacterial contamination-resistant carboxylate-plus-polymer compositions herein can be used in the manufacture of a wide variety of medical devices, especially urinary catheters, intravenous catheters, wound dressings, and the like.

4 Claims, No Drawings

ANTIMICROBIAL POLYMER COMPOSITIONS

TECHNICAL FIELD

Catheterization of humans and lower animals is required in the treatment of a variety of disease states. Yet, because catheters provide a direct path from the environment into the patient's body, the risk of bacterial or mycotic contamination and sepsis is especially acute when patients are catheterized.

Decisions regarding catheterization of the urinary bladder and prolonged endotracheal intubation (for respiratory support) are always influenced by considerations of the high risk of infection occasioned by prolonged contact of these foreign objects (the catheter) with mucosal surfaces where pathogenic bacteria and fungi are normally present.

Similarly, a wide variety of surgical conditions require the insertion of drains or catheters into normally inaccessible parts of the body through artificial, surgically-created passages. Examples include pneumothorax, hydrocephalus, and biliary tract surgery. In these cases, although an infection is less likely, it is usually a serious complication when it occurs so that patients with these problems are frequently treated with prophylactic courses of antibiotics, with the attendant risks of allergy, toxicity, superinfection and development of resistant strains of bacteria.

Physicians have long decried the fact that progress in developing treatment regimens for burn victims, comatose patients, patients who have undergone gastrointestinal surgery, cancer victims, and other patients whose natural barriers to infection have been compromised is being hindered by the problem of sepsis.

" . . . [H]alf of all nosocomial infections were related to devices used to treat patients . . . " Dr. Dennis Maki, *The New York Times,* June 5, 1978.

Physicians are apparently meeting this problem by curtailing or even discontinuing the portion of their therapeutic regimen which involves interruption of the body's antimicrobial barriers by foreign objects such as urinary catheters, and the like. Even when such devices are employed, as they frequently are, the attendant high risk of infection is always a consideration which enters physicians' evaluation of the risk/benefit ratio of the chosen course of therapy.

Another approach has been the widespread adoption of more stringent sterility and "good housekeeping" standards for hospitals. Unfortunately, fungi and bacteria remain ubiquitous in the hospital environment. However, even most pathogenic bacteria and fungi are harmless to humans and lower animals unless the body's natural barriers to infection break down. This can occur by a break in skin integrity as in a surgical incision or the insertion of an intravenous catheter, or by the interference of a foreign body with the group of normal flora which inhabit the mucous membranes and other epithelialized areas of the body as in the case of urinary catheters. Current hypotheses hold that infectious microorganisms migrate from the point of entry into the body inward along catheters, drains, and the like, until they reach the bloodstream or other tissues which provide a fertile medium for growth. But regardless of the route, once infectious microorganisms are internalized, massive infestation throughout the body can result.

Bacterial sepsis can generally be treated successfully with antibiotics, but a complete treatment regimen can be expensive and time consuming. In addition, antibiotic therapy is often complicated by superinfections and, increasingly, the appearance of antibiotic-resistant pathogenic strains. Mycotic infections (fungi, molds, yeasts), typically occasioned by extremely high fevers, are unusually refractory to commonly employed antibiotics and as a result are often fatal.

In light of the foregoing, it is clear that when a break in the body's natural barriers to infection is necessary, prevention of infection is always preferable to treatment.

From the foregoing it can also be seen that an ideal method of preventing the infections associated with the use of catheters and similar medical devices is to establish an antimicrobial barrier on the surface of and around such devices, so that bacteria are unable to migrate along them and into the body.

The present invention provides a method of preventing nosocomial infections resulting from the use of catheters by achieving microbial inhibition at and around the catheter placement site.

This is achieved by using catheters fashioned from the novel, antimicrobial polymer compositions disclosed herein.

The polymers of this invention are also suitable for other (especially medical) uses where prolonged freedom from bacterial contamination is required. For example, the polymers of this invention can be used as bandages, wrappings, wound dressings, incontinence pads, implantable prosthetic devices, and self-sterilizing parts for mechanical respiratory care equipment, pump-oxygenators, and the like.

BACKGROUND ART

The use of antimicrobials to inhibit the growth of bacteria, fungi and molds in food compositions for oral ingestion is well known. For example, sodium propionate is routinely added to commerical bread to inhibit mold. In spite of the body of literature on this general topic, workers in the medical/veterinary sciences do not appear to have appreciated the special benefits which are afforded when carboxylate antimicrobials are used in the manner of the present invention. In particular, the incorporation of carboxylate antimicrobials in the polymers of the present type, thereby allowing diffusion of the antimicrobial agent from devices fashioned from said polymers and providing a zone of microbial inhibition on tissue surfaces surrounding said devices, has not been suggested heretofore. This is indeed surprising, in light of the pressing need to avoid microbial contamination and possible sepsis in patients undergoing treatment regimens where there is any likelihood of direct communication between the external environment and normally protected tissues and the body cavities.

This oversight on the part of the medical community may have occurred because medical science is only now coming to grips with the problem of massive sepsis due to newer medical techniques. Equally likely is that the carboxylates have been passed over as ineffective antimicrobials in light of the confused state of recent literature.

The doctoral dissertation of Roger L. Stone, entitled "The Requirements for Metabolizable Energy and Nitrogen for Maintenance in Parenterally Fed Sheep", The Ohio State University, published August, 1975, page 37, discloses the use of propionic acid in intravenous solutions. These solutions were administered via a silicone rubber catheter, but no mention is made of any antimicrobial effect of the acid-plus-catheter combination, nor was the silicone rubber impregnated with the propionic acid.

U.S. Pat. No. 2,729,586, issued Jan. 3, 1956 to S. M. Peck, describes therapeutic compositions comprising water-soluble chlorophyll and at least one salt of a $C_3$-$C_{11}$ monocarboxylic acid.

U.S. Pat. No. 4,002,775, issued Jan. 11, 1977, to J. J. Kabara, describes fatty acids and derivatives as antimicrobial agents. According to the Kabara patent, neither caproic (hexanoic) nor caprylic (octanoic) acid are inhibitory to any of the microorganisms under the test conditions. Yet, properly used in the manner disclosed herein, these two carboxylate materials have now been found to be particularly potent, yet safe and highly preferred, antimicrobial agents which are capable of prolonged diffusion from polymers, especially silicone elastomers, to provide a zone of microbial inhibition around catheters, and the like.

U.S. Pat. No. 2,154,449, Hoffman, et al., 1939, describes the use of aliphatic carboxylic acids ($C_3$-$C_{12}$) or their salts as mold inhibitors in foods. The patent teaches the use of these acids to protect materials susceptible to mold, including tobacco, paper, leather, textiles, etc.

U.S. Pat. No. 2,190,714, to Hoffman, et al., 1940, claims a method of inhibiting mold growth in food products other than margarine and sour dough bread by adding a $C_3$-$C_{12}$ carboxylic acid thereto.

U.S. Pat. No. 3,404,987, to Kooistra and Troller, 1968, discloses and claims an antimicrobial composition containing 110 parts by weight of an edible mineral salt (iron, manganese, zinc, tin, or silver) and 1-150 parts by weight of an edible acid preservative substance, specifically including propionic acid. The metal salts are taught to impart enhanced and sustained antimicrobial/antifungal activity to the acid preservative substance.

U.S. Pat. No. 1,772,975, Wieland, 1930, teaches the use of solutions of lactic acid, acetic acid, or homologues thereof, as antiseptics at properly adjusted pH's.

U.S. Pat. No. 3,466,663, Russ, et al., 1949, describes the use of caprylic (octanoic) acid to combat mycotic infections of growths. This acid may be used topically as a liquid, ointment or butter for the treatment of surface infectants. It is also taught to be useful for combatting internal infections by injecting intravenously.

The Merck Index, 7th Ed., page 1117, teaches that zinc propionate is used as a fungicide on adhesive tape to reduce plastic irritation caused by molds, fungi and bacterial action.

German Patent No. 2,720,776, issued Nov. 23, 1978 to Akiyama, describes a urinary catheter for long-term use which is made of an elastomer or polymer and which gives off bactericidal metal ions.

U.S. Pat. No. 3,434,869, issued Mar. 25, 1969 to J. B. Davidson, describes a urinary catheter of organic rubber with a surface coating of elastomeric silicone containing a silica filler.

U.S. Pat. No. 3,598,127, issued Aug. 10, 1971 to J. G. Wepsic, describes a catheter having an inner tube of non-permeable rubber formed with V-shaped grooves extending along its length on the outside, carrying antibacterial agents permeable through polysiloxane rubber that surrounds the V-shaped grooves. The antibacterials mentioned in this patent include neomycin, bacitracin, sulfa, mandelamine, zephiran, hexachlorophene, and furadantoin.

Numerous patents cover catheters and similar articles of various designs and materials. Examples include the following.

U.S. Pat. No. 3,699,956, to S. Kitrilakis, et al., Oct. 24, 1972, discloses a percutaneous lead device including an element for preventing bacterial infection caused by implanting the lead through the skin.

U.S. Pat. No. 3,695,921, issued Oct. 3, 1972, to T. H. Shepherd, et al., describes a catheter provided with a coating of a hydrophilic acrylate or methacrylate polymer. Infection from the catheter is said to be further reduced by absorbing an antibiotic such as penicillin, bacitracin, and others, or an antibacterial such as hexachlorophene, or a quaternary ammonium compound, in the coating. See also U.S. Pat. No. 3,566,874, issued Mar. 2, 1971.

U.S. Pat. No. 3,663,965, issued May 23, 1972, to H. L. Lee, et al., describes a bacteria-resistant percutaneous conduit device.

U.S. Pat. No. 3,524,447, issued Aug. 18, 1970, to R. P. Evans, et al., discloses a method of making a rigid tipped polyvinyl catheter.

U.S. Pat. No. 3,598,126, issued Aug. 10, 1971, to J. Hoeltzenbein, describes a vascular cannula for medical applications.

U.S. Pat. No. 3,708,324, issued Jan. 2, 1973, to L. F. Stebleton, discloses a method of growing silicone elastomers useful in the manufacture of catheters.

U.S. Pat. No. 3,926,705, issued Dec. 16, 1975, to D. A. Todd, discloses a "Silicone Catheter and Process for Manufacturing Same." See also U.S. Pat. No. 3,983,879.

U.S. Pat. No. 3,886,947, issued June 3, 1975, to P. N. Sawyer, describes a non-thrombogenic catheter.

Belgian Patent No. 857,264, issued Jan. 30, 1978, to R. L. Stone, describes intravenous solutions comprising aqueous solutions of $C_4$-$C_9$ n-fatty acid antimicrobials. It is the equivalent of copending U.S. application Ser. No. 816,625, filed July 18, 1977, which is a continuation-in-part of application Ser. No. 709,342, filed July 28, 1976, now abandoned.

Copending application Ser. No. 918,532, R. L. Stone, filed June 23, 1978, also discloses solutions containing $C_4$-$C_9$ fatty acid antimicrobials.

As can be seen from the foregoing, various means for providing antimicrobial catheters have been employed heretofore. The present invention employs safe, highly effective carboxylate antimicrobial agents in various known, medical grade polymers to achieve the results sought by prior workers in the field more safely, simply and economically than previously believed possible. In addition, the antimicrobial polymers of the present invention can be used to manufacture all types of medical devices, and are not limited in their utility to special catheter configurations.

Prior art catheters have also often had the problem of too-rapid release of antimicrobial agent under typical usage conditions. The present invention provides antimicrobial polymer compositions from which release of the antimicrobial can be controlled to provide sustained antimicrobial activity over long periods of use.

DISCLOSURE OF INVENTION

The present invention comprises, as a composition of matter: a polymer, said polymer having releasably incorporated within the polymer matrix a safe and effective amount of a carboxylate antimicrobial agent, or mixtures thereof, said polymer optionally containing from 0% to about 40% by weight of a substantially non-antimicrobial proton donor. When such compositions are to be fashioned into articles for use in the bodies of humans or lower animals, the component materials should be toxicologically acceptable.

The preferred polymers employed herein are the toxicologically-acceptable, medical grade silicone elastomers well known in the medical arts.

The preferred carboxylate antimicrobial agents used herein are the $C_3$–$C_{11}$ n-alkane and alkene monocarboxylates, especially the $C_4$–$C_{10}$ n-alkane monocarboxylates, most preferably the $C_6$–$C_{10}$ n-alkane monocarboxylates. In their acid form, these carboxylates have a broad spectrum of kill for the types of bacteria and fungi most often found in hospitals, are safe to humans and lower animals, and are compatible with the polymers used herein.

The carboxylate antimicrobial/polymer compositions of the present invention are more useful in medical devices such as catheters than prior art "bactericidal" catheters since the antimicrobial activity of catheters of the present invention continues for prolonged periods (days or weeks) and provides the added benefit of antifungal activity. The rate of release of the carboxylate antimicrobial agent can optionally be adjusted according to the needs of the user by incorporating certain toxicologically-acceptable, substantially non-antimicrobial proton donors into the polymer matrix. Such proton donor materials include, for example, citric acid (preferred), tartaric acid, malic acid, fumaric acid, maleic acid, malonic acid, ascorbic acid and barbituric acid, and mixtures thereof.

The antimicrobial/polymers of the present invention can be used in the manufacture of all manner of medical devices, including endotracheal tubes, wound and burn dressings, implantable prostheses, heart valves, etc., and are especially suitable for the manufacture of intravenous catheters and urinary catheters. Medical devices manufactured from the instant antimicrobial polymers are also emcompassed by this invention.

The invention herein also provides a method for catheterization of humans and lower animals with lowered risk of nosocomial infection by achieving microbial inhibition at and around the placement site of catheters and the like used in the bodies of humans and lower animals, comprising: inserting into the body of a human or lower animal in need of such treatment a catheter, or the like, said catheter comprising: delivery means for transporting liquid materials, such delivery means being in the form of a tube; at least part of the portion of said tube which contacts the body comprising a carboxylate antimicrobial/polymer composition according to this invention.

The present invention also provides a means for manufacturing polymers having a controlled rate of release of carboxylate antimicrobial agents of the type disclosed herein, comprising incorporating said antimicrobial agent into said polymer and, after the polymer matrix containing the carboxylate antimicrobial is wholly (preferred) or partially cured, heating said polymer to a temperature of about 100° C., or higher, in contact with moisture; for example, in a steam autoclave, or like apparatus.

By "carboxylate antimicrobial agent" herein is meant the $C_3$–$C_{11}$, inclusive, n-alkane and alkene monocarboxylic acids and their water-soluble salts, and mixtures thereof. It is to be understood that either the acids or their salts may be employed in the compositions and methods of this invention, although the free acid RCOOH, where R is $C_2$–$C_{10}$ n-alkane or alkene, is the active antimicrobial moiety.

By "substantially non-antimicrobial proton donor" herein is meant a Lowry-Bronsted acid which does not exhibit substantial antimicrobial activity at the concentrations employed herein.

By "zone of microbial inhibition" or "zone of inhibition" herein is meant a region containing a sufficient concentration of antimicrobial agent that growth and reproduction of viable microorganisms within the zone is halted.

By "nosocomial infection" herein is meant an infection, either systemic or localized, acquired as a result of hospitalization or treatment while hospitalized, or acquired incident to medical therapy.

By "safe and effective amount" is meant an amount of antimicrobial carboxylate and/or mixture of antimicrobial-plus-proton donor which is effective to produce a zone of microbial inhibition around the polymer compositions herein and yet causes no undesirable side effects (at a reasonable benefit/risk ratio) when the compositions are used in contact with living tissue.

By "medical grade" herein is meant of a quality, purity, etc., suitable and/or approved for medical use.

By "autoclaving" herein is meant subjecting to superheated steam under pressure.

By "in-line device" herein is meant a device adapted for introduction in series into the fluid path of a fluid flow system, so that all of the fluid passing through that portion of the system passes through the device.

Best Mode

The antimicrobial/polymers compositions of the present invention can be manufactured by various means. In one mode, the polymer, conveniently in the form of the desired medical device such as a catheter, is simply soaked in the pure carboxylic acid antimicrobial agent. The antimicrobial carboxylic acid perfuses the polymer matrix, and is released, in use, in a patient.

In another mode, a water-soluble salt (e.g., sodium salt) of the antimicrobial carboxylic acid is added to the polymer in the pre-curing stage. The polymer is thereafter cured and can be fashioned into any desired type of device.

The manufacture of the instant polymers using either of the foregoing methods is effective for some purposes, but is sub-optimal when prolonged release of the antimicrobial carboxylic acid from the catheter is desired. Soaking the polymer in the carboxylic acid leads to a product which releases that carboxylic acid over a time course of a few hours. Simply adding the sodium salt form of the acid to the polymer matrix yields a product which releases the antimicrobial carboxylic acid so slowly that operable, but sub-optimal, antimicrobial results are secured.

Either of two manufacturing methods can be used to achieve the desired, prolonged release of antimicrobially-effective amounts of the carboxylic acid antimicrobial agents from the polymers herein. In the first procedure, a water-soluble salt of the carboxylic acid is incorporated into the pre-polymer matrix (e.g., prior to curing) together with a substantially non-antimicrobial proton donor (e.g., citric acid). The pre-polymer mass is then shaped to any desired configuration and polymerized to entrap the carboxylate and proton donor in the polymer matrix. The conjoint use of the two materials in the polymer matrix provides the desired prolonged release, yet the release rate is rapid enough that antimicrobial efficacy on the surface of the polymer and on surrounding tissue surfaces is achieved.

Alternatively, the water-soluble salt of the carboxylic acid antimicrobial agent is incorporated into the prepolymer (e.g., at the pre-cured stage); the polymer is then shaped and cured, thereby entrapping the salt in the polymer matrix. The polymer matrix is thereafter heated, preferably in contact with water (conveniently, by steam autoclaving) and an article which releases the carboxylate antimicrobial agent over a prolonged period is secured. Optionally, a non-antimicrobial proton donor can be co-entrapped in the polymer matrix with the salt of the antimicrobial carboxylic acid in this mode of manufacture. While not intending to be limited by theory, it appears that contacting the polymer matrix (especially medical grade silicone polymers) with steam partially solubilizes the carboxylate salt in the matrix and possibly partially hydrolyzes the carboxylate salt to the free acid form. The antimicrobial release from the polymer matrix is desirably modified and prolonged.

Highly preferred carboxylate-permeable polymers for preparing the compositions of the present invention are the commercially-available silicones, especially the medical grade polydimethylsiloxanes manufactured under "clean" conditions and marketed for various medical uses. Such silicones are safe for prolonged use in contact with human tissues and provide excellent diffusion of the preferred n-octanoic and n-decanoic acid carboxylate antimicrobials used herein. As is well known in the art, the silicone polymers can readily be fashioned into catheters and other medical devices designed for a variety of applications. Typical examples of such silicone materials are Silastic® 382 and Dow Corning® MDX® 4-4210, MDX® 4-4515, MDX® 4-4516 and Q® 7-2213, all available from the Dow Corning Corporation.

The following examples further illustrate the preferred mode of practicing the invention using steam autoclaving and the added proton donor material to secure prolonged release of the antimicrobial agent from the polymer.

EXAMPLE I

A polydimethylsiloxane composition releasably containing sodium decanoate as the antimicrobial is prepared as follows.

595.8 grams of Dow Corning® MDX® 4-4210 clean grade elastomer is available in two parts: an elastomer base and a curing agent which, when mixed and cured, form the finished silicone polymer. 595.8 Grams of the elastomer base are poured into a stainless steel mixing bowl, along with 59.6 grams of the catalyst (curing agent) and 45 grams powdered sodium n-decanoate. This combination is mixed at low shear (to avoid excessive entrainment of air) until the sodium decanoate powder is uniformly dispersed throughout the mixture. The mixture is then deaerated in a vacuum chamber until no more entrapped air can be seen. The composition is then injected into a mold cavity of appropriate shape for forming, for example, urinary catheters, ear prostheses, respirator valves, and the like. The silicone material is cured by heating in the mold at about 125° C. for at least about 15 minutes.

After the foregoing molded silicone/decanoate device is cured it is placed in a commercial steam autoclave (120°–130° C.) for a period of ca. 10 minutes. The device is then ready for use in the body of a human or lower animal patient.

Medical devices of the foregoing type exhibit an effective antimicrobial barrier for a period of several days at their external surfaces and in tissues immediately surrounding the site of insertion into the bodies of humans and lower animals.

EXAMPLE II

A polymer is prepared in the manner of Example I by admixing the following components: 600 g. Dow Corning® MDX® 4-4210 clean grade elastomer; 59.6 g. curing agent; 20 g. citric acid; and 38 g. sodium octanoate. In use, urinary and i.v. catheters manufactured from the silicone/citric acid/octanoate polymer exhibit an effective antimicrobial barrier for a period up to several days at their external surfaces and in tissues immediately surrounding the site of insertion into the bodies of humans and lower animals. Optionally, the catheters can be steam autoclaved prior to use.

In preferred silicone polymer compositions of the present type the carboxylate antimicrobial (i.e., the free acid or a water-soluble salt) will generally comprise from about 5% to about 25% by weight of the total composition, the balance comprising the silicone polymer matrix. In compositions comprising the carboxylate salt plus proton donor, the weight ratio of carboxylate salt:proton donor can vary within a wide range (e.g., 1000:1 to 1:1000; conveniently 1:1) and the rate of release of antimicrobial can be adjusted by adjusting this ratio. Preferably, the mixture of carboxylate and proton donor will comprise from about 5% to about 25% of the composition, the balance comprising the polymer matrix.

The preferred carboxylates used herein are sodium n-octanoate and sodium n-decanoate. The preferred proton donor is citric acid.

All percentages and ratios herein are by weight, unless otherwise specified.

Industrial Applicability

The compositions of the present invention comprise polymers having releasably incorporated within the polymer matrix a safe and effective amount of a carboxylate antimicrobial agent, or mixtures thereof. The polymers can also contain from 0% to about 40% by weight of a substantially non-antimicrobial proton donor. Variations on the fundamental principles of this invention may be undertaken without departing from the scope and spirit thereof, as more fully described hereinafter.

Polymeric Materials

When the compositions of this invention are to be used in contact with body fluids and tissues, the polymer portion of the composition (and the total composition or device made therefrom) should be toxicologically acceptable. Moreover, the overall device, including the polymer, will most preferably by immunologically acceptable and will not be rejected by the body's natural defense mechanisms nor have any untoward effect on the rate of antibody formation, and the like.

The polymeric materials should be substantially water insoluble so that they maintain their strength and integrity when in contact with body fluids and similar aqueous environments. Articles made from the compositions of the present invention are preferably fashioned substantially completely from the composition. Thus, the polymeric material should be capable of satisfying the mechanical requirements of its intended use, but selection of appropriate polymers is not a problem.

However, not all polymer materials are acceptable for use as the polymer in the compositions of the present invention, although in manufacturing medical devices, non-permeable polymers can be used as part of the overall device. In order to distinguish those polymer materials useful in the practice of the present invention without undue experimentation, it is only necessary to conduct the Zone of Inhibition Test, hereinafter described, on the desired polymer material.

Zone of Inhibition Testing

*Candida albicans* are cultured in a yeast nitrogen-based broth (Difco ®) for 24 hours. Sabouraud Dextrose Agar (Difco ®) is prepared, and 0.1 ml. of the 24-hour *C. albicans* culture is added per 100 ml. of the agar.

Strips of the polymer to be tested are stretched across standard 5-inch petri dishes on edge. Around the strips is poured the agar seeded with *C. albicans*.

The agar is permitted to gel and the petri dishes are incubated at 37° C. for 24 hours. The plates are then examined microbiologically for zones of microbial inhibition surrounding the polymer strips. For evaluating the antimicrobial spectrum of the polymer compositions of this invention, identical tests are conducted using Trypticase ® (Baltimore Biological Laboratories) soy agar seeded with *Staphylococcus aureus*, representative of gram positive bacteria, and *Pseudomonas aeruginosa*, representative of gram negative bacteria.

Any composition of antimicrobial-containing polymer which produces a zone of inhibition in this simple test, regardless of the width of the zone, is suitable for use herein as a "carboxylic acid-permeable polymer". Polydimethylsiloxanes not only produce excellent zones of inhibition, they provide such high-level sustained release of antimicrobial that actual cidal zones, i.e., zones of no growth, are obtained in the foregoing test.

It can be seen from the foregoing test that polymers suitable for use in the compositions of the present invention can readily and easily be selected using the zone of inhibition criteria.

The compositions of the present invention preferably comprise silicone polymers as the polymeric material. The silicone polymers used in preparing the preferred compositions of this invention are polydimethylsiloxane, which may contain side chain branching and cross linking, as well as various functional groups to facilitate cross linking/curing.

Silicone polymers suitable for use herein can be prepared, for example, by hydrolyzing dimethyldichlorosilane or mixtures of dimethyldichlorosilane, trichloromethylsilane and chlorotrimethylsilane with water, in well known fashion. Alternatively, siloxane "oligomers" can be polymerized and "cured" in various ways well known in the art. Silicone polymers suitable for preparing the catheters of the present invention are also available commercially, in medical grade purity, from suppliers such as the Dow Corning Corporation and the General Electric Company.

Latex rubbers can also be used as the polymer in the compositions of the present invention. Either the natural or synthetic latex rubber polymers which are commercially available can be used. Such materials include, for example, the isoprene-type rubbers, and the like. Natural or synthetic rubber which is calendered or molded can also be used.

Other types of polymers which can be used in the compositions of the present invention comprise, for example, polyurethanes; copolymers of silicone polymers and various other polymeric materials such as urethanes, and the like; certain styrene/butadiene copolymers; etc.

Carboxylate Antimicrobials

The antimicrobial agents used herein ("carboxylate antimicrobials") are selected from the non-aromatic water-soluble $C_3$–$C_{11}$ n-alkane and alkene carboxylic acids, or mixtures thereof, or any of their water-soluble, pharmaceutically-acceptable salts. Such salts include, for example, the common water-soluble sodium, potassium, ammonium, etc., salts. The sodium and potassium salts are preferred.

While various carboxylate compounds exhibit different degrees of antimicrobial activity (per mole) in the practice of this invention, the water-soluble n-alkane $C_3$, $C_4$, $C_5$, $C_6$, $C_7$, $C_8$, $C_9$, $C_{10}$ and $C_{11}$ carboxylates exhibit excellent antimicrobial activity.

The microbiocidal activity of the $C_3$–$C_{11}$ carboxylate antimicrobials used herein is directly related to the presence of their respective free acids. The concentration of free carboxylic acid, as opposed to carboxylate salt (anionic) form, is a function of pH. Accordingly, the amount of acid or acid salt which must be used will vary somewhat with the use pH. The amount of a given acid or acid salt which will provide a zone of inhibition at a given pH will depend on the pKa of the acid. Of course, knowing the pKa, the minimum inhibitory or minimum lethal concentration of the particular acid and the use pH, the amount of any $C_3$–$C_{11}$ acid or acid salt to be used is easily calculated from the formula $$pKa = pH + \log [HC_x]/[C_x-],$$

where $[HC_x]$ is the concentration of free acid of chain length x and $[C_x-]$ is the concentration of its anion.

The $MLC_{30\,sec.}$ values for the n-butyric, n-pentanoic, n-hexanoic, n-heptanoic and n-nonanoic acids are as follows: $C_4$ 0.4 molar; $C_5$ 0.11 M; $C_6$ 30 mM; $C_7$ 9 mM; $C_9$ 1 mM. Decanoic, undecanoic and undecylenic acids, while effective, are essentially water-insoluble, so that their $MLC_{30\,sec.}$ values cannot be measured in aqueous systems.

When the carboxylate antimicrobial is used in the form of a water-soluble salt, it is necessary to disperse the salt in particulate form throughout the polymer composition. Carboxylate salt particles which are too large produce surface blebs in the polymer material, which make articles made therefrom undesirably rough. Accordingly, the particles of carboxylate salt used in the compositions of this invention preferably will have diameters of less than 500 microns. Most preferred are truly "micronized" particles, i.e., particles having diameters in the range of from 0.1-10 microns.

Many water-soluble salts of the $C_3$–$C_{11}$ n-carboxylic acids have a "soapy" texture and thus are difficult to reduce to micron-range particles. An excellent, preferred method for producing readily dispersible, micronizable particles of the carboxylate antimicrobial salts is freeze-drying, by standard techniques and using commercially-available equipment.

As mentioned hereinafter, some polymer/carboxylate compositions swell undesirably in contact with water. It will be found that the smaller the carboxylate salt particle size, the greater the degree of polymer swelling produced; however, the smaller the particle size of the carboxylate salt in the composition, the more amenable the composition is to reduction of swelling by autoclaving, as hereinafter described, so that this phenomenon is not a problem.

Antimicrobial Concentration

One of the variables in the formulation of compositions of the present invention is the concentration of the dispersed antimicrobial in the polymer. For example, the influence of the "loading concentration" of sodium n-octanoate in silicone rubber can be observed by measuring the zones of inhibition of Candida growth in agar surrounding silicone-octanoate strips. Large increases in zone sizes were observed with increasing octanoate concentrations.

Release experiments were conducted by measuring desorption into water from 2×2 cm. silicone rubber sheets containing different quantities of Na $^{14}$C-octanoate. The thicknesses of the sheets were 1 mm. The observed release rates are tabulated below:

| $^{14}$C-Octanoate Concentration | Release Rate (ug/√hr.) at 37° C. |
| --- | --- |
| 6% | 224 |
| 10% | 473 |
| 15% | 7,520 |

The foregoing release rates all provide acceptable microbial inhibition (bacteria and fungi) at the surface of the polymer and in the surrounding area. Accordingly, it can be seen that the release rate of antimicrobials can be varied simply by varying the concentration of antimicrobial agent in the polymer matrix. In general, concentrations of from about 0.01% to about 60% of the carboxylate antimicrobial (or mixture of carboxylate-plus-proton donor) are used. Concentrations higher than about 60% may undesirably affect the structural integrity of the polymers. (This, of course, will depend on the desired end-use of the polymer. For example, a bandage pad need not be as strong as a catheter.) Some polymers will tolerate levels above 60%. For most purposes 10-30% antimicrobial are adequate to provide antimicrobial efficacy for many days. Knowing the release rate and the content of antimicrobial in the polymer, the time period over which the polymer will remain sterile in use can be calculated.

Autoclaving

While not intending to be limited by theory, the polymer materials which incorporate water-soluble salts of the antimicrobially-effective n-alkane monocarboxylic acids appear to work by an ion-exchange mechanism, i.e., protons from the polymer matrix are exchanged for the cationic moiety of the salt (e.g., sodium), and the protonated acid thus formed is able to diffuse through the polymer matrix to the surface to form a zone of microbial inhibition.

Autoclaving appears to accelerate this ion-exchange process. Indeed, the enhancement of release rates by autoclaving surpasses the effects of other variables for enhancing release of antimicrobial, including concentration variation of the "loading" concentration, changes in the density of crosslinking in a polymer, the effect of minor variations in polymer molecular weight, and the effect of particle size on release rate. The quantitative effect of autoclaving is so substantial that an inadequate formulation (characterized by an initial pulse of released material diminishing very quickly to a negligible release rate lasting more than a year) is directly converted to a formulation releasing rapidly in less than the expected clinical time frame. Thus, a wide range of antimicrobial release rates can be provided by steam treatment of a given formulation for times which vary from 1 to up to 60 minutes. With the preferred silicone polymers, the effect of autoclaving is suspected to involve solubilization of the carboxylate salt in the polymer matrix, and possibly some depolymerization of the polydimethylsiloxane chains, thereby increasing the n-carboxylic acid and water permeabilities of the polymer and enhancing the carboxylic acid antimicrobial release rate.

Some polymers, especially polydimethyl siloxanes, containing n-carboxylic acid antimicrobials or, especially, their pharmaceutical salts, undesirably swell when the polymer formulation comes in contact with water. A reduction in polymer swelling by increased cross-linking density can be achieved by increasing the ratio of cross-linking agent to monomer during formulation, and also by increasing the curing temperature. Increasing the cross-linking agent by 2 or 4-fold reduces swelling to 18-22%. Increasing cure temperature further reduces swelling, but only marginally. However, increased cure temperature alone results in a swelling reduction of 24%. Thus, nearly the same swelling decrease can be obtained by increased cure temperature using a recommended proportion of cross-linking agent. However, it has now been unexpectedly discovered that autoclaving (120°-130° C.; steam pressure ~20 psi) for at least 15 minutes prior to use, in addition to having a beneficial effect on antimicrobial release, also markedly reduces swelling of the silicone/carboxylate polymer compositions to a negligible level.

Proton Donors

The substantially non-antimicrobial proton donors which can optionally be used in the present compositions preferably comprise low molecular weight, toxicologically-acceptable organic acids which are solids at room temperature. Non-limiting examples of such acids include: citric, ascorbic, tartaric, malic, fumaric, maleic, malonic, and barbituric acids, and mixtures thereof. Liquid acids tend to diffuse rapidly from the polymers and are thereby lost as proton sources for converting the n-carboxylate salts to the active free acids. Thus, liquid acids are not preferred as the non-antimicrobial proton donors herein.

Aryl acids, such as salicylic and benzoic acids, undesirably interfere with the matrix structure and/or curing of some polymers useful in the compositions of this invention, and thus are not preferred.

The following examples are intended to further illustrate the practice of this invention, but are not intended to be limiting thereof.

EXAMPLE III

DuPont Hytrel ® polyester is fashioned by standard techniques into discs 30 mm. in diameter and 0.3 mm. thick, for use as one-way check valves in anesthesia breathing circuits. The discs are immersed for 48 hours in a bath of liquid n-hexanoic acid. The discs are then removed, wiped dry and packaged in sterile containers or incorporated directly into anesthesia equipment.

Sample discs, when cut into strips, produce excellent zones of microbial inhibition in plates of *C. albicans,* or similarly prepared plates containing *Staphylococcus aureus* or *Pseudomonas aeruginosa*. In use, the hexanoic acid diffusing from the Hytrel ® polyester material prevents microbial contamination of the anesthesia check valves, and thus helps to prevent cross contamination of respiratory pathogens between surgical patients.

In the foregoing example, the Hytrel ® polyester is replaced with any of the following materials: Shell Elexar ® butadiene-styrene copolymer; Steven ® 1880 (MP)CRG polyurethane (ether base); and Uniroyal ® TPR 1900 ethylenepropylene copolymer. Equivalent results are secured.

EXAMPLE IV 77.23 Grams of polydimethylsiloxane are mixed in the liquid state with 18.1 grams of citric acid, 31.6 grams freeze-dried, micronized (1-10 micron diameter) potassium hexanoate, and 85.8 grams of a peroxide catalyst (curing agent). The composition is stirred until the citric acid and potassium hexanoate are uniformly dispersed throughout the mixture, and the mixture is then deaerated under vacuum. The polymer is fashioned into ventriculostomy catheters of standard design and cured by heating at 115° C. or greater for approximately 30 minutes. The ventriculostomy catheters are steam autoclaved for 30 minutes and packaged in sterile containers for use.

In use, the potassium hexanoate is partially converted to hexanoic acid within the polymer matrix, and gradually diffuses to the surface of the catheter to provide continuing antimicrobial action, providing added protection against infection for the patient undergoing ventriculostomy.

The compositions of this invention can be used in the manufacture of an in-line device especially adapted for releasing an antimicrobial agent, or the like, into a fluid flow system, comprising: (a) a container fitted with inlet and outlet means for said fluid; and (b) within said container, one or more discrete bodies comprising a polymer composition according to this invention, as illustrated in the following example.

EXAMPLE V

Silicone rubber is formulated in the manner of the foregoing examples to contain 200 mg./cm$^3$ valeric (pentanoic) acid. The rubber is molded into beads 3–4 mm. in diameter, and the beads are packed into a cylindrical plastic housing 3 cm. in diameter $\times$ 10 cm. long, fitted with a "luer" inlet connector at one end and a "luer" outlet connector at the other end. The device is sterilized and packaged for use. In use, the device is interposed in the fluid path of an intravenous infusion set and the valeric acid released into the infusion fluid during its passage through the device provides antimicrobial activity against accidentally introduced contaminants.

The device of the foregoing example is used with intravenous infusions administered to a dog, and excellent results are secured.

EXAMPLE VI

A 10 meter roll of 0.25 mm. thick $\times$ 10 cm. wide Steven ® MP1880 CRG polyurethane film is immersed in a bath of n-nonanoic acid for 48 hours. The nonanoic acid enters the polymer to the extent of about 40% by weight.

The film is used as a liner tape prior to application of a standard plaster walking cast of the ankle. The nonanoic acid incorporated into the polyurethane tape provides sustained protection against fungal and bacterial infections of the skin covered by the cast.

EXAMPLE VII

The foregoing polyurethane material containing nonanoic acid is fashioned into microperforate sheets as non-wettable outer liners for incontinence pads filled with absorbent cellulose fibers. The nonanoic acid released slowly from the outer liner prevents bacterial and fungal contamination of the pad in use.

What is claimed is:

1. A composition of matter, comprising: a toxicologically-acceptable, medical-grade elastomeric polymer, said polymer having releasably incorporated within the polymer matrix a safe and effective amount of one or more free n-alkane monocarboxylic acid antimicrobial agents or salts thereof, having from about 4 to about 10 carbon atoms, said polymer containing from about 0.1% to about 40% by weight of a substantially non-antimicrobial proton donor selected from the group consisting of citric acid, tartaric acid, malic acid, fumaric acid, maleic acid, malonic acid, ascorbic acid, barbituric acid, and mixtures thereof.

2. A composition according to claim 1 wherein the antimicrobial agent is in the form of one or more pharmaceutically-acceptable alkali metal salts of the n-alkane monocarboxylic acid and comprises from about 0.01% to about 60% by weight of the composition.

3. A composition according to claim 1, wherein the antimicrobial agent is selected from the group consisting of octanoic acid, sodium octanoate, or mixtures thereof.

4. A composition according to claim 1 wherein the antimicrobial agent comprises from about 0.01% to about 60% by weight of the composition.

* * * * *